United States Patent
Suehara et al.

(10) Patent No.: US 11,661,374 B2
(45) Date of Patent: *May 30, 2023

(54) CHEMICALLY-STRENGTHENED GLASS

(71) Applicant: AGC Inc., Tokyo (JP)

(72) Inventors: Michinori Suehara, Tokyo (JP); Yusuke Fujiwara, Tokyo (JP); Lilin Zhou, Tokyo (JP)

(73) Assignee: AGC Inc., Tokyo (JP)

(*) Notice: Subject to any disclaimer, the term of this patent is extended or adjusted under 35 U.S.C. 154(b) by 120 days.

This patent is subject to a terminal disclaimer.

(21) Appl. No.: 17/205,703

(22) Filed: Mar. 18, 2021

(65) Prior Publication Data
US 2021/0206691 A1    Jul. 8, 2021

Related U.S. Application Data

(63) Continuation of application No. 16/720,521, filed on Dec. 19, 2019, now Pat. No. 11,427,503, which is a (Continued)

(30) Foreign Application Priority Data

Jun. 23, 2017   (JP) .............. JP2017-123365

(51) Int. Cl.
*C03C 21/00* (2006.01)
*G02B 1/14* (2015.01)
(Continued)

(52) U.S. Cl.
CPC ............. *C03C 21/002* (2013.01); *G01N 3/24* (2013.01); *G01N 3/56* (2013.01); *G01N 33/386* (2013.01);
(Continued)

(58) Field of Classification Search
CPC ... C03C 21/002; C03C 2204/08; C03C 3/085; C03C 3/091; C03C 15/00; G01N 3/24;
(Continued)

(56) References Cited

U.S. PATENT DOCUMENTS

2011/0165393 A1   7/2011   Bayne et al.
2015/0052949 A1   2/2015   Bayne et al.
(Continued)

FOREIGN PATENT DOCUMENTS

EP   0 933 377 A2   8/1999
JP   2000-144097 A   5/2000
(Continued)

OTHER PUBLICATIONS

International Search Report dated Sep. 18, 2018 in PCT/JP2018/023536 filed Jun. 20, 2018 (with English Translation), 5 pages.
(Continued)

*Primary Examiner* — Nathan L Van Sell
(74) *Attorney, Agent, or Firm* — Oblon, McClelland, Maier & Neustadt, L.L.P.

(57) ABSTRACT

The purpose of the present invention is to provide a chemically-strengthened glass exhibiting both surface strength and abrasion-resistant anti-fingerprint (AFP) properties. The present invention relates to a plate-shaped chemically-strengthened glass which has a compressive stress layer provided to a glass surface layer, a glass surface hydrogen concentration profile in a specific range, and a surface strength and abrasion-resistant anti-fingerprint (AFP) properties which are in specific ranges.

8 Claims, 4 Drawing Sheets

Related U.S. Application Data continuation of application No. PCT/JP2018/023536, filed on Jun. 20, 2018.

(51) Int. Cl.
  *G02B 1/18* (2015.01)
  *G01N 3/24* (2006.01)
  *G01N 3/56* (2006.01)
  *G01N 33/38* (2006.01)
  *H05K 5/00* (2006.01)
  *H05K 5/03* (2006.01)

(52) U.S. Cl.
  CPC .................. *G02B 1/14* (2015.01); *G02B 1/18* (2015.01); *H05K 5/0017* (2013.01); *H05K 5/03* (2013.01)

(58) Field of Classification Search
  CPC .................. G01N 3/56; G01N 33/386; G01N 2203/0067; G01N 2203/0282; G01N 3/20; G01N 2203/0005; G02B 1/14; G02B 1/18; H05K 5/0017; H05K 5/03
  See application file for complete search history.

(56) References Cited

U.S. PATENT DOCUMENTS

| | | |
|---|---|---|
| 2016/0130178 A1 | 5/2016 | Kashima et al. |
| 2016/0130179 A1 | 5/2016 | Kashima et al. |
| 2016/0207828 A1 | 7/2016 | Kashima et al. |
| 2018/0072619 A1 | 3/2018 | Kashima et al. |

FOREIGN PATENT DOCUMENTS

| | | |
|---|---|---|
| JP | 2011-197708 A | 10/2011 |
| JP | 2013-516387 A | 5/2013 |
| JP | 2016-132598 A | 7/2016 |
| JP | 2016-142600 A | 8/2016 |
| WO | WO 2015/008766 A1 | 1/2015 |
| WO | WO 2017/115765 A1 | 7/2017 |

OTHER PUBLICATIONS

Han, W-T. et al., "Effect of residual water in silica glass on static fatigue," Journal of Non-Crystalline Solids, vol. 127, 1991, 5 pages.
Ilievski, S. et al., "Practical IR extinction coefficients for water in commercial glasses determined by nuclear reaction analysis," Glastech. Ber. Glass Sci. Technol., vol. 73, No. 2, 2000, 4 pages.

CHEMICALLY-STRENGTHENED GLASS

CROSS REFERENCE TO RELATED APPLICATIONS

The present application is a continuation of U.S. patent application Ser. No. 16/720,521, filed on Dec. 19, 2019, which is a continuation of PCT/JP2018/023536, filed on Jun. 20, 2018, which claims priority to Japanese patent application JP 2017-123365, filed Jun. 23, 2017.

TECHNICAL FIELD

The present invention relates to a chemically strengthened glass.

BACKGROUND ART

In recent years, chemically strengthened glasses have been used as cover glasses of various display devices. It is requested to further improve the strength thereof. Conventionally, it has been known that a glass is immersed in a molten salt of potassium nitrate or the like to thereby perform a chemical strengthening treatment on the glass in order to enhance the surface strength of the glass. For example, Patent Literature 1 discloses that a glass is immersed in a molten salt of potassium nitrate to thereby perform a chemical strengthening treatment on the glass in order to enhance the surface strength of the glass sheet. In addition, Patent Literature 1 discloses that the glass sheet subjected to the chemical strengthening treatment is then subjected to a surface etching treatment, in order to further improve the surface strength of the glass sheet subjected to the chemical strengthening treatment.

On the other hand, in order to attain reduction in weight and reduction in thickness, a so-called OGS (One Glass Solution) type display device has been developed (Patent Literature 2). In the OGS type display device, a chemically strengthened glass is equipped directly with touch sensors to omit a glass sheet, and the chemically strengthened glass equipped with the touch sensors is disposed on a liquid crystal display (LCD).

In order to impart an antifouling property, a scratch resistance property, a surface slip property and a function of reducing adhesion of fingerprints, a surface of a chemically strengthened glass may be coated with an AFP (Anti Finger Print) agent including a silicone-based compound, a fluorine-based compound or a composition containing those compounds by a method such as deposition, spraying or dipping, so as to form an AFP film (Patent Literature 3). An excellent abrasion-resistant property of the AFP film is required so that the desired antifouling property, scratch resistance property, surface slip property and function of reducing adhesion of fingerprints can be sustained for a long time.

CITATION LIST

Patent Literature

Patent Literature 1: JP-A-2013-516387
Patent Literature 2: JP-A-2011-197708
Patent Literature 3: JP-A-2000-144097

SUMMARY OF INVENTION

Technical Problem

However, in the chemically strengthened glass obtained by the manufacturing method described in Patent Literature 1, there is a problem that abrasion-resistant property of the AFP film formed with the AFP agent applied to the glass surface (hereinafter also referred to as "AFP abrasion resistance") is so low that the surface strength is not sufficient.

Therefore, in consideration of the aforementioned circumstances, an object of the present invention is to provide an unconventional chemically strengthened glass having both surface strength and AFP abrasion resistance.

Solution to Problem

The present inventors have made extensive and intensive investigations. As a result, it has been found that surface strength and AFP abrasion resistance can be attained compatibly in a chemically strengthened glass in which a hydrogen concentration profile in a surface layer is within a specific range, hereby leading to accomplishment of the present invention.

That is, the present invention relates to the following configurations.

1. A chemically strengthened glass having a sheet shape and including a compressive stress layer in a glass surface layer, in which:

a straight line linearly approximating a profile of a hydrogen concentration Y with respect to a depth X from an outermost surface of a glass sheet at X=0.1 to 0.6 (μm) satisfies Expression (I);

a surface strength F (N) measured on conditions below by a ball-on-ring strength test satisfies a relation of $F \geq 1500 \times t^2$ with respect to a sheet thickness t (mm) of the glass sheet; and a contact angle is 65° or more after 4,000 times of an abrasion when an AFP abrasion resistance is measured on conditions below by a rubber eraser abrasion test:

$$Y = aX + b \tag{I}$$

in which:
Y is the hydrogen concentration (mol/L, measured as $H_2O$);
X is the depth from the outermost surface of the glass sheet (μm);
a is −0.450 to −0.300; and
b is 0.250 to 0.400, Ball-on-Ring (BoR) Strength Test Conditions:

a glass sheet having a sheet thickness t (mm) is disposed on a stainless steel ring having a diameter of 30 mm and including a contact portion rounded with a curvature radius of 2.5 mm, and a steel ball having a diameter of 10 mm is brought into contact with the glass sheet; in this state, the ball is loaded at a center of the ring under static load conditions; a breaking load (in units of N) at which the glass is broken is regarded as a BOR strength, and an average value of 20 times measurements of the BOR strength is regarded as a surface strength F; here, a case where a breaking start point of the glass is 2 mm or more away from a loading point of the ball is excluded from data for calculating the average value, Rubber Eraser Abrasion Test Conditions:

a chemically strengthened glass sheet surface is cleaned by ultraviolet rays, and sprayed and coated with OPTOOL (registered trademark) DSX (made by Daikin Industries, Ltd.) so as to form an AFP film substantially uniformly on the glass sheet surface;

a rubber eraser (MINOAN™ made by Mirae Science Co., Ltd.) is attached to an indenter with 1 $cm^2$ wide; in a state where a load of 1 kgf is applied to the rubber eraser, an AFP film surface formed on the glass sheet surface is rubbed with the rubber eraser reciprocatively 4,000 times with a stroke width of 20 mm and at a velocity of 30 mm/sec; then, the AFP film surface is dry-wiped and cleaned with a cloth (DUSPER (registered trademark) made by Ozu Corporation); thereafter, water contact angles (°) are measured at three places on the AFP film surface; this operation is repeated three times, and an average water contact angle (°) is measured from a total of nine water contact angles; the water contact angles (°) on the AFP film surface are measured by a method according to JIS R 3257 (1999).

2. The chemically strengthened glass according to the aforementioned configuration 1, having a surface roughness (Ra) of 0.30 nm or more.

3. The chemically strengthened glass according to the aforementioned configuration 1 or 2, having a surface compressive stress value (CS) of 600 MPa or more.

4. The chemically strengthened glass according to any one of the aforementioned configurations 1 through 3, having a depth of the compressive stress layer (DOL) of 10 μm or more.

5. The chemically strengthened glass according to any one of the aforementioned configurations 1 through 4, having an internal tensile stress (CT) of 72 MPa or less.

6. The chemically strengthened glass according to any one of the aforementioned configurations 1 through 5, which is used as a cover glass of a display device.

Advantageous Effects of Invention

According to the present invention, it is possible to provide a chemically strengthened glass having both surface strength and AFP abrasion resistance owing to a profile of hydrogen concentration in a glass sheet surface layer set within a specific range.

DESCRIPTION OF EMBODIMENTS

Figure 1:
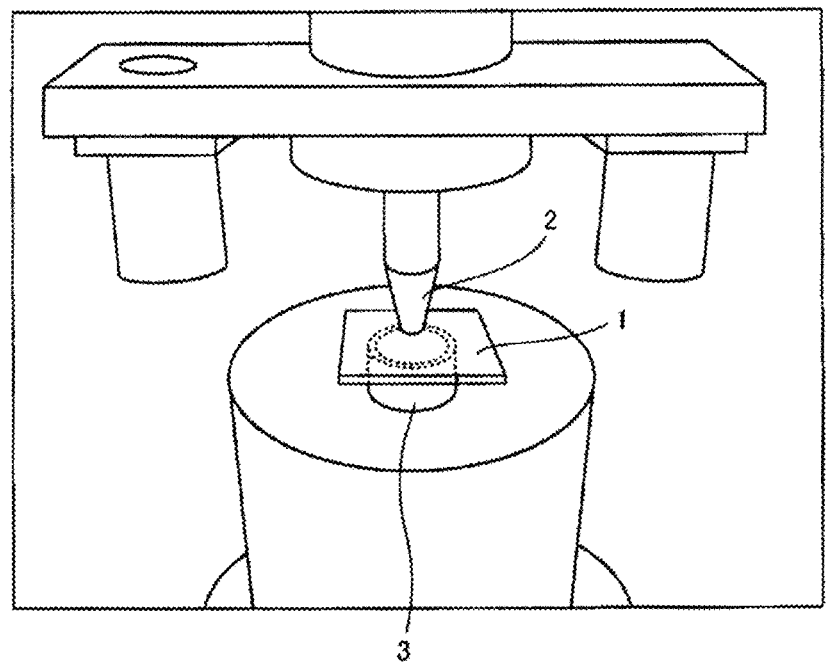
FIG. 1 is a schematic view illustrating a method of a ball-on-ring strength test.

The present invention will be described below in detail. However, the present invention is not limited to the following embodiments, and may be modified desirably to carry out without departing from the gist thereof. In addition, the word "to" designating a numerical range in the present description is used as a denotation of a range including numerical values on both sides of the word "to" as a lower limit value and an upper limit value of the range. In addition, in the present description, "mass %" and "mass ppm" are synonyms for "weight %" and "weight ppm" respectively. In addition, "ppm" written simply means "weight ppm".

<Chemically Strengthened Glass>

The chemically strengthened glass of the present invention is a chemically strengthened glass including a compressive stress layer in a glass sheet surface layer formed by ion exchange, in which:

a straight line linearly approximating a profile of a hydrogen concentration Y with respect to a depth X from an outermost surface of a glass sheet at X=0.1 to 0.6 (μm) satisfies Expression (I);

a surface strength F (N) measured on conditions below by a ball-on-ring strength test satisfies a relation of $F \geq 1500 \times t^2$ with respect to a sheet thickness t (mm) of the glass sheet; and a contact angle is 65° or more after 4,000 times of an abrasion when an AFP abrasion resistance is measured on conditions below by a rubber eraser abrasion test.

$$Y=aX+b \qquad (I),$$

in which:

Y is the hydrogen concentration (mol/L, measured as $H_2O$);

X is the depth from the outermost surface of the glass sheet (μm);

a is −0.450 to −0.300; and b is 0.250 to 0.400.

Ball-on-Ring (BoR) Strength Test Conditions:

A glass sheet having a sheet thickness t (mm) is disposed on a stainless steel ring having a diameter of 30 mm and including a contact portion rounded with a curvature radius of 2.5 mm, and a steel ball having a diameter of 10 mm is brought into contact with the glass sheet. In this state, the ball is loaded at a center of the ring under static load conditions. A breaking load (in units of N) at which the glass is broken is regarded as a BOR strength, and an average value of 20 times measurements of the BOR strength is regarded as a surface strength F. Here, a case where a breaking start point of the glass is 2 mm or more away from a loading point of the ball is excluded from data for calculating the average value.

Rubber Eraser Abrasion Test Conditions:

A chemically strengthened glass sheet surface is cleaned by ultraviolet rays, and sprayed and coated with OPTOOL (registered trademark) DSX (made by Daikin Industries, Ltd.) so as to form an AFP film substantially uniformly on the glass sheet surface.

A rubber eraser (MINOAN™ made by Mirae Science Co., Ltd.) is attached to an indenter with 1 $cm^2$ wide. In a state where a load of 1 kgf is applied to the rubber eraser, an AFP film surface formed on the glass sheet surface is rubbed with the rubber eraser reciprocatively 4,000 times with a stroke width of 20 mm and at a velocity of 30 mm/sec. Then, the AFP film surface is dry-wiped and cleaned with a cloth (DUSPER (registered trademark) made by Ozu Corporation). Thereafter, water contact angles (°) are measured at three places on the AFP film surface. This operation is repeated three times, and an average water contact angle (°) is measured from a total of nine water contact angles. The water contact angles (°) on the AFP film surface are measured by a method according to JIS R 3257 (1999).

The chemically strengthened glass according to the present invention has an ion-exchanged compressive stress layer in the glass sheet surface layer. In the present description, the compressive stress layer is a high density layer formed by bringing the glass sheet into contact with inorganic salt such as potassium nitrate to cause ion exchange between metal ions (Na ions) in the glass surface and ions (K ions) having large ionic radii in the inorganic salt. Owing to the increase of density in the glass sheet surface, a compressive stress is generated so that the glass sheet can be strengthened.

(Glass Composition)

It will go well if a glass for use in the present invention contains alkali ions. Glasses having various compositions can be used as long as they have components capable of being formed and strengthened by a chemical strengthening treatment. Among them, the glass preferably contains sodium. Specific examples of such glasses include aluminosilicate glass, soda lime glass, borosilicate glass, lead glass, alkali barium glass, and aluminoborosilicate glass.

Although the composition of a glass for use as the chemically strengthened glass according to the present invention is not particularly limited, the following glass compositions may be used, for example.

(1) A glass containing 50 to 74% of $SiO_2$, 1 to 15% of $Al_2O_3$, 6 to 18% of $Na_2O$, 0 to 3% of $K_2O$, 2 to 15% of MgO, 0 to 6% of CaO, 0-5% of $ZrO_2$, and 0 to 1% of $TiO_2$ as a composition expressed by mol % on an oxide basis, where a total content of $SiO_2$ and $Al_2O_3$ is 76% or less, and a total content of $Na_2O$ and $K_2O$ is 12 to 25%.

(2) A glass containing 55.5 to 80% of $SiO_2$, 8 to 20% of $Al_2O_3$, 8 to 25% of $Na_2O$, 0 to 3% of $K_2O$, 0 to 1% of $TiO_2$, 0-5% of $ZrO_2$, and 1% or more of alkaline earth metal RO (RO designates MgO+CaO+SrO+BaO) as a composition expressed by mol % on an oxide basis.

(3) A glass containing 56 to 72% of $SiO_2$, 8 to 20% of $Al_2O_3$, 3 to 20% of $B_2O_3$, 8 to 25% of $Na_2O$, 0 to 5% of $K_2O$, 0 to 15% of MgO, 0 to 15% of CaO, and 0 to 1% of $TiO_2$ as a composition expressed by mol % on an oxide basis.

(4) A glass containing 60 to 72% of $SiO_2$, 1 to 18% of $Al_2O_3$, 1 to 5% of MgO, 0 to 5% of CaO, 12 to 19% of $Na_2O$, and 0 to 5% of $K_2O$, and containing 1% or more of alkaline earth metal RO (RO designates MgO+CaO+SrO+BaO), as a composition expressed by mass % on an oxide basis.

(5) A glass containing 55.5 to 80% of $SiO_2$, 12 to 20% of $Al_2O_3$, 8 to 25% of $Na_2O$, 2.5% or more of $P_2O_5$, and 1% or more of alkaline earth metal RO (RO designates MgO+CaO+SrO+BaO) as a composition expressed by mol % on an oxide basis.

(6) A glass containing 57 to 76.5% of $SiO_2$, 12 to 18% of $Al_2O_3$, 8 to 25% of $Na_2O$, 2.5 to 10% of $P_2O_5$, and 1% or more of alkaline earth metal RO as a composition expressed by mol % on an oxide basis.

(7) A glass containing 56 to 72% of $SiO_2$, 8 to 20% of $Al_2O_3$, 3 to 20% of $B_2O_3$, 8 to 25% of $Na_2O$, 0 to 5% of $K_2O$, 0 to 15% of MgO, 0 to 15% of CaO, 0-15% of $SrO_2$, 0 to 15% of BaO, and 0 to 8% of $ZrO_2$ as a composition expressed by mol % on an oxide basis.

(Hydrogen Concentration)

In the chemically strengthened glass according to the present invention, a profile of a hydrogen concentration in a glass sheet surface layer is within a specific range. Specifically, a straight line obtained by linearly approximating a profile of a hydrogen concentration Y with respect to a depth X from an outermost surface of the glass sheet at X=0.1 to 0.6 (μm) satisfies the following Expression (I).

$$Y=aX+b \quad (I)$$

signs in Expression (I) have the following meanings respectively:

Y: hydrogen concentration (mol/L, measured as $H_2O$);
X: depth from the outermost surface of the glass sheet (μm);
a: −0.450 to −0.300; and
b: 0.250 to 0.400]

As for the strength of a glass sheet, it has been known that the strength of the glass sheet is lowered by the existence of hydrogen (moisture) in the glass. The present inventors found that the strength of a glass may be lowered after a chemical strengthening treatment, and the major cause of that is due to the fact that moisture in the atmosphere intrudes the glass to cause chemical defects.

When a glass has a high hydrogen concentration, hydrogen enters an Si—O—Si bond network of the glass to form Si—OH bond. Thus, the Si—O—Si bond is disconnected. As the hydrogen concentration in the glass is higher, it can be considered that parts where the Si—O—Si bond is disconnected are increased, and thus chemical defects tend to be generated to lower the strength.

The aforementioned Expression (I) is established in the region of the depth X=0.1 to 0.6 (μm) from the outermost surface of the glass sheet. The thickness of a compressive stress layer formed by ion exchange depends on the degree of chemical strengthening, but it is normally formed within a range of from 5 to 90 μm. The intrusion depth of hydrogen into the glass depends on a diffusion coefficient, temperature and time, and the intrusion amount of hydrogen depends on the moisture amount in the atmosphere in addition to those factors. The hydrogen concentration after the chemical strengthening is the highest in the outermost surface and decreases gradually toward a deeper portion (bulk) where the compressive stress layer is not formed. The decreasing degree of the hydrogen concentration is prescribed in the aforementioned Expression (I). In the outermost surface (X=0 μm), the moisture concentration is likely to vary due to deterioration with time. Therefore, it is assumed that Expression (I) is established in a near-surface region (X=0.1 to 0.6 (μm)) which is assumed not to be affected by the variation of the moisture concentration in the outermost surface.

In Expression (I), a designates an inclination prescribing the decreasing degree of the hydrogen concentration. The range of a is −0.450 to −0.300, preferably −0.380 to −0.300, and more preferably −0.350 to −0.300. On the other hand, in Expression (I), b corresponds to the hydrogen concentration at the outermost surface (X=0 μm). The range of b is 0.250 to 0.400, preferably 0.250 to 0.370, and more preferably 0.250 to 0.320.

Generally it is considered that a very small crack existing in a surface of a glass sheet is extended by external mechanical pressure, thereby causing reduction in strength of the glass sheet. As the glass structure at the tip of the crack is richer in Si—OH, the crack is extended more easily (Won-Taek Han et al., "Effect of residual water in silica glass on static fatigue", Journal of Non-Crystalline Solids, 127, (1991) 97-104). On the assumption that the tip of the crack is exposed to the atmosphere, it is estimated that the Si—OH content at the tip of the crack indicates a positive correlation with the hydrogen concentration in the outermost surface of the glass. Accordingly, it is preferable that b corresponding to the hydrogen concentration in the outermost surface is preferably within the aforementioned range.

The intrusion depth of hydrogen is highly likely to vary depending on the conditions of the chemical strengthening treatment. However, on the assumption that the intrusion depth of hydrogen does not vary, a negative correlation appears between b corresponding to the hydrogen concentration in the outermost surface and a corresponding to the inclination prescribing the decreasing degree of the hydrogen concentration. It is therefore preferable that a is preferably within the aforementioned range.

(Method for Measuring Hydrogen Concentration Profile)

Here, the hydrogen concentration profile ($H_2O$ concentration, mol/L) of the glass sheet is a profile measured under the following analysis conditions.

Secondary ion mass spectrometry (SIMS) is used for measuring the hydrogen concentration profile of the glass sheet. To obtain a quantitative hydrogen concentration profile by the SIMS, a standard specimen whose hydrogen concentration has been known is required. A method for preparing a standard specimen and a method for quantitatively determining a hydrogen concentration will be described below.

1) A part of a glass sheet to be measured is cut out.
2) A region at least 50 μm deep from a surface of the glass sheet thus cut out is removed by polishing or chemical etching. Removing treatment is performed on both the opposite sides of the glass sheet. That is, the removed thickness is at least 100 μm in total on the opposite sides. The glass sheet subjected to the removing treatment is regarded as a standard specimen.
3) Infrared spectroscopy (IR) is applied to the standard specimen to obtain absorbance height $A_{3550}$ of a peak top near 3,550 cm$^{-1}$ and absorbance height $A_{4000}$ at 4,000 cm$^{-1}$ (base line) in an IR spectrum.
4) A sheet thickness d (cm) of the standard specimen is measured using a sheet thickness meter such as a micrometer.
5) With reference to Literature A, the hydrogen concentration (mol/L, measured as $H_2O$) of the standard specimen is obtained using the following Expression (II) on the assumption that the infrared practical absorbance index $\varepsilon_{pract}$ (L/(mol·cm)) of $H_2O$ in the glass is 75.

Hydrogen concentration of standard specimen=
$(A_{3550} - A_{4000})/(\varepsilon_{pract} \cdot d)$     Expression (II)

Literature A) S. Ilievski et al., Glastech. Ber. Glass Sci. Technol., 73 (2000) 39.

The glass sheet to be measured and the standard specimen with the known hydrogen concentration obtained by the aforementioned method are conveyed into an SIMS apparatus simultaneously, and measured sequentially to obtain depth-direction profiles of $^1H^-$ and $^{30}Si^-$ intensities. After that, the $^1H^-$ profile is divided by the $^{30}Si^-$ profile to obtain a depth-direction profile of the $^1H^-/^{30}Si^-$ intensity ratio. From the depth-direction profile of the $^1H^-/^{30}Si^-$ intensity ratio in the standard specimen, an average $^1H^-/^{30}Si^-$ intensity ratio in a depth region of from 0.1 μm to 0.6 μm is calculated, and a calibration curve between the value of the average $^1H^-/^{30}Si^-$ intensity ratio and the hydrogen concentration is created to pass through an origin (calibration curve on single standard specimen). By use of the calibration curve, the $^1H^-/^{30}Si^-$ intensity ratio in the ordinate of the profile of the glass sheet to be measured is converted into hydrogen concentration. Thus, a hydrogen concentration profile of the glass sheet to be measured is obtained. Incidentally, SIMS and IR measuring conditions will be described below.

(Measuring Conditions of SIMS)
Apparatus: ADEPT1010 made by ULVAC-PHI, Incorporated
Primary Ion Species: Cs$^+$
Primary Ion Acceleration Voltage: 5 kV
Primary Ion Current Value: 500 nA
Primary Ion Incident Angle: 60° with respect to normal line of specimen surface
Primary Ion Raster Size: 300×300 μm$^2$
Secondary Ion Polarity: minus
Secondary Ion Detection Region: 60×60 μm$^2$ (4% of primary ion raster size)
ESA Input Lens: 0
Use of Neutralization Gun: yes Method for Converting Abscissa from Sputtering Time to Depth: Depth of an analysis crater is measured by a stylus type surface shape measuring instrument (Dektak 150 made by Veeco Instruments Inc.) to obtain a primary ion sputtering rate. By use of this sputtering rate, the abscissa is converted from the sputtering time to the depth.

Field Axis Potential upon $^1H^-$ detection: An optimum value may vary depending on the apparatus. A measurer sets the value carefully to cut the background sufficiently.

(Measuring Conditions of IR)
Apparatus: Nic-plan/Nicolet 6700 made by Thermo Fisher Scientific Inc.
Resolution: 8 cm$^{-1}$
Integration: 64
Detector: TGS detector From the hydrogen concentration profile ($H_2O$ concentration, mol/L) of the glass sheet measured under the aforementioned analysis conditions, Expression (I) is derived in the following procedure. Linear approximation is performed on the profile of the hydrogen concentration Y in the region of the depth X=0.1 to 0.6 (μm) from the outermost surface of the glass sheet. An expression of an approximate straight line obtained thus is set as Expression (I).

Examples of means for controlling a and b include changing the concentration of flux, the concentration of sodium, the temperature, the time, etc. in the chemical strengthening treatment.

(Strength of Glass Sheet)

The strength (surface strength) of the chemically strengthened glass sheet according to the present invention can be evaluated by a BoR (Ball-on-Ring) strength test. Specifically the BoR strength test is performed as follows.

The chemically strengthened glass according to the present invention is evaluated by BoR strength F (N) measured by a BoR strength test performed as follows. That is, a glass sheet with a sheet thickness t (mm) is placed on a ring-like reception jig having a diameter of 30 mm. The ring-like reception jig is made of stainless steel and includes a contact portion rounded with a curvature radius of 2.5 mm. In a state where a pressure jig 2 (made of quenched steel, sphere having a diameter of 10 mm and mirror-finished) made of SUS304 is brought into contact with the glass sheet, the pressure jig 2 is loaded at the center of the ring-like reception jig under static load conditions.

FIG. 1 shows a schematic view for explaining the BoR strength test used in the present invention. In the BoR strength test, a glass sheet 1 which has been mounted horizontally is pressurized by use of the pressure jig 2 (made of quenched steel, having a diameter of 10 mm, and mirror-finished) which is a ball made of SUS304. Thus, the strength of the glass sheet 1 is measured.

In FIG. 1, the glass sheet 1 which serves as a sample is placed horizontally on the reception jig 3 (having a diameter of 30 mm, including a contact portion having a curvature radius R of 2.5 mm and made of quenched steel, and mirror-finished) made of SUS304. The pressure jig 2 for pressurizing the glass sheet 1 is placed above the glass sheet 1.

In the present embodiment, the central region of the glass sheet 1 obtained in each of Examples and Comparative Examples is pressurized from above the glass sheet 1. Incidentally, test conditions will be described below.

Descending Rate of Pressure Jig 2: 1.0 (mm/min)

On this occasion, a breaking load (in units of N) with which the glass sheet is broken is regarded as BoR strength, and an average value of BoR strength measured 20 times is regarded as BoR average strength. When a breaking start point of the glass sheet is 2 mm or more away from the position where the ball is pressed, the measured BoR strength is excluded from data for calculating the average value.

The chemically strengthened glass according to the present invention satisfies the relation of $F \geq 1500 \times t^2$, more preferably the relation of $F \geq 1800 \times t^2$, even more preferably the relation of $F \geq 2000 \times t^2$, and particularly preferably the relation of $F \geq 2100 \times t^2$. (In the expression, F designates BoR strength (N) measured by the BoR strength test, and t designates the sheet thickness (mm) of the glass sheet.). When the BoR strength F (N) is within such a range, the chemically strengthened glass can exhibit excellent strength even if it is formed into a thin sheet.

(AFP Abrasion Resistance)

The AFP abrasion resistance in the chemically strengthened glass according to the present invention can be evaluated by the following rubber eraser abrasion test.

(Rubber Eraser Abrasion Test)
Test Conditions:

A surface of a chemically strengthened glass sheet is cleaned by ultraviolet rays, and sprayed and coated with OPTOOL (registered trademark) DSX (made by Daikin Industries, Ltd.) so as to form an AFP film substantially uniformly on the glass sheet surface.

A rubber eraser (MINOAN™ made by Mirae Science Co., Ltd.) is attached to an indenter with 1 cm² wide. In a state where a load of 1 kgf is applied to the rubber eraser, the surface of the AFP film formed on the glass sheet surface is rubbed with the rubber eraser reciprocatively 4,000 times with a stroke width of 20 mm and at a velocity of 30 mm/sec. After that, the AFP film surface is dry-wiped and cleaned with a cloth (DUSPER (registered trademark) made by Ozu Corporation). Then, water contact angles (°) are measured at three places on the AFP film surface. This operation is repeated three times, and an average water contact angle (°) is measured from the total of nine water contact angles.

The water contact angles (°) on the AFP film surface are measured by a method according to JIS R 3257 (1999).

The aforementioned rubber eraser abrasion test can be performed by use of a commercially available tester (for example, plane abrasion tester (triple type) model: PA-300A made by Daiei Kagaku Seiki Mfg. Co., Ltd.) or the like.

In the chemically strengthened glass according to the present invention, the AFP abrasion resistance measured under the aforementioned conditions by the rubber eraser abrasion test is 65° or more, preferably 70° or more, more preferably 75° or more, and particularly preferably 80° or more in contact angle after 4,000 times of rubbing. When the contact angle is 65° or more, an excellent antifouling property, an excellent scratch resistance property and an excellent surface slip property can be sustained for a long time. It is more preferable that the contact angle is larger. However, the contact angle may be 125° or less as an upper limit value thereof.

The chemically strengthened glass according to the present invention can exhibit excellent AFP abrasion resistance in various situations when the AFP abrasion resistance measured under the aforementioned conditions by the aforementioned rubber eraser abrasion test is within the aforementioned range.

(Surface Roughness)

In the chemically strengthened glass according to the present invention, surface roughness (Ra) is preferably 0.30 nm or more, more preferably 0.40 nm or more, and even more preferably 0.50 nm or more in order to enhance the AFP abrasion resistance. When the surface roughness is 0.30 nm or more, the AFP abrasion resistance can be enhanced. It is more preferable that the surface roughness (Ra) is higher. However, the surface roughness may be 2.0 nm or less, preferably 1.5 nm or less, and more preferably 1.0 nm or less as an upper limit value thereof. When the surface roughness (Ra) is made 2.0 nm or less, it is possible to prevent white cloudiness of the glass to thereby suppress deterioration in quality of its appearance. The surface roughness is measured in a 1 μm×0.5 μm measurement region by AFM (Atomic Force Microscope) surface observation.

(Depth of Compressive Stress Layer, and Surface Compressive Stress Value)

The compressive stress layer is a high density layer formed by ion exchange between Na ions in the glass surface and K ions in a molten salt when the glass is brought into contact with the inorganic salt such as potassium nitrate.

The depth of the compressive stress layer (DOL) can be measured by use of an EPMA (Electron Probe Micro Analyzer), a surface stress meter (e.g. FSM-6000 made by Orihara Industrial Co., Ltd.) or the like.

In the chemically strengthened glass according to the present invention, the depth of the compressive stress layer is preferably 10 μm or more, more preferably 15 μm or more, even more preferably 20 μm or more, and particularly preferably 25 μm or more in order to provide sufficient strength to the glass. On the other hand, the upper limit of the depth of the compressive stress layer is not particularly limited, but is typically 140 μm or less.

The thickness of a low-density layer to be removed by an acid treatment step or an alkali treatment step which will be described later is from about 10 nm to about 1,000 nm at the most. Accordingly, as for the depth of the compressive stress layer in the chemically strengthened glass according to the present invention, the depth of the compressive stress layer formed in the chemical strengthening treatment is substantially equal to the depth of the compressive stress layer which has been subjected to the acid treatment step or the alkali treatment step.

The surface compressive stress value (CS) of the chemically strengthened glass according to the present invention is preferably 600 MPa or more, more preferably 650 MPa or more, even more preferably 700 MPa or more, and particularly preferably 800 MPa or more. On the other hand, although the upper limit is not particularly limited, the surface compressive stress value is typically 1,400 MPa or less.

The surface compressive stress value can be measured by use of an EPMA (Electron Probe Micro Analyzer), a surface stress meter (e.g. FSM-6000 made by Orihara Industrial Co., Ltd.) or the like. The surface compressive stress value can be calculated by use of a stress profile calculation method disclosed in JP-A-2016-142600.

The internal tensile stress (CT) of the chemically strengthened glass according to the present invention is preferably 72 MPa or less, more preferably 62 MPa or less, and even more preferably 52 MPa or less. On the other hand, although the lower limit is not particularly limited, the internal tensile stress is typically 20 MPa or more. A CT value is obtained in such a manner that a stress distribution is measured, and the obtained stress distribution is integrated by thickness.

<Method for Manufacturing Chemically Strengthened Glass>

As a method for manufacturing a chemically strengthened glass according to the present invention, a method including the following steps (a) to (d) can be exemplified.

(a) a step of preparing a glass sheet containing alkali ions;
(b) a step of preparing inorganic salt containing other alkali ions larger in ionic radii than the alkali ions contained in the glass sheet;
(c) a step of performing ion exchange between the alkali ions in the glass sheet and the other alkali ions in the inorganic salt in an atmosphere with a dew point of 20° C. or higher; and
(d) a step of removing a part of the ion-exchanged surface of the glass sheet Each of the steps will be described below.

((a) Step of Preparing a Glass Sheet Containing Alkali Ions)

Although a method for manufacturing a glass is not particularly limited, the glass can be manufactured as follows. A desired glass raw materials are put into a continuous melting furnace. The glass raw materials are heated and melted preferably at 1,500 to 1,600° C., and clarified. After that, the molten glass is supplied to a forming apparatus and formed into a sheet-like shape, then followed by being gradually cooled.

Incidentally, various methods can be used for forming the glass sheet. Examples of the forming methods include a down draw process (such as an overflow down draw process, a slot down process, a redraw process, etc.), a float process, a roll-out process, a press process, etc. Among those processes, the float process is preferred. Because in the float process, at least a part of a glass sheet surface may be cracked, and therefore the effect of the present invention can be confirmed conspicuously.

The sheet thickness of the glass sheet is not particularly limited. However, in order to perform the chemical strengthening treatment effectively, the thickness is normally preferably 5 mm or less, more preferably 3 mm or less, even more preferably 1 mm or less, and particularly preferably 0.7 mm or less.

In addition, the shape of the glass sheet used in the present invention is not particularly limited. For example, glass sheets having various shapes such as a flat sheet shape with a uniform sheet thickness, a shape with a curved surface in at least one of the front surface and the back surface, a cubic shape with a bent portion or the like, etc. can be used.

((b) Step of Preparing Inorganic Salt Containing Other Alkali Ions Larger in Ionic Radii than the Alkali Ions Contained in the Glass Sheet)

The chemically strengthened glass according to the present invention has an ion-exchanged compressive stress layer in the glass sheet surface layer. In an ion exchange process, the surface of the glass sheet is ion-exchanged to form a surface layer where a compressive stress remains. Specifically, alkali metal ions (Li ions and/or Na ions) with small ionic radii in the glass sheet surface are substituted with other alkali ions (Na ions and/or K ions) with larger ionic radii by ion exchange at a temperature equal to or lower than a glass transition point. Thus, the compressive stress remains on the surface of the glass sheet, and the strength of the glass sheet is improved.

As the method for manufacturing a chemically strengthened glass according to the present invention, a chemical strengthening treatment is carried out by ion exchange in which a glass containing alkali ions as described previously is brought into contact with inorganic salt containing other alkali ions with larger ionic radii than the alkali ions contained in the glass. That is, the alkali ions contained in the glass are ion-exchanged with the other alkali ions contained in the inorganic salt.

When the alkali ions contained in the glass are Na ions, it is preferable that the inorganic salt contains potassium nitrate ($KNO_3$). It is more preferable that the inorganic salt further contains at least one kind of salt selected from the group consisting of $K_2CO_3$, $Na_2CO_3$, $KHCO_3$, $NaHCO_3$, $Li_2CO_3$, $Rb_2CO_3$, $Cs_2CO_3$, $MgCO_3$, $CaCO_3$, and $BaCO_3$.

For example, when the inorganic salt contains potassium nitrate, the potassium nitrate has a melting point at 330° C., which is not higher than the strain point (normally 500 to 600° C.) of the glass to be chemically strengthened. In addition, the aforementioned salts excluding the potassium nitrate (hereinafter also referred to as "flux") has a property of disconnecting a network of the glass represented by Si—O—Si bond. The temperature at which the chemical strengthening treatment is performed is several hundred ° C., which is so high that Si—O covalent bonds of the glass are cut suitably at the temperature. Thus, a density reduction treatment which will be described later tends to proceed.

Incidentally, the degree of cutting of the covalent bonds differs depending on the conditions of the chemical strengthening treatment, such as the glass composition, the kind of the salt (flux), the temperature or the time for the chemical strengthening treatment, etc. However, it is considered that it is preferable to select conditions with which, of four covalent bonds extending from Si, one or two bonds can be cut.

A high density compressive stress layer is formed by ion exchange between Na ions (or Li ions) in the glass sheet surface and K ions (or Na ions) in the inorganic salt. As a method for bringing the glass sheet into contact with the inorganic salt, a method for applying the paste-like inorganic salt to the glass, a method for spraying an aqueous solution of the inorganic salt to the glass, a method for immersing the glass into a salt bath of the molten salt heated to the melting point thereof or higher, etc. can be used. Among them, the method for immersing the glass into the molten salt is preferred.

The inorganic salt may contain, in addition to the potassium nitrate and the flux, other chemical species as long as they do not impede the effect of the present invention. Examples of the other chemical species include alkali chloride or alkali borate such as sodium chloride, potassium chloride, sodium borate, potassium borate. One of those may be added alone, or some kinds of them may be added in combination.

In the molten salt used in the method for manufacturing the chemically strengthened glass according to the present invention, the Na concentration is preferably 500 weight ppm or more, and more preferably 1,000 weight ppm or more. It is further more preferable that the Na concentration in the molten salt is 2,000 weight ppm or more because the low density layer can be made deeper by the acid treatment step which will be described later. The upper limit of the Na concentration is not particularly limited, but it is allowed to be high enough to obtain a desired surface compressive stress (CS).

((c) Step of Performing Ion Exchange Between the Alkali Ions in the Glass Sheet and the Other Alkali Ions in the Inorganic Salt in an Atmosphere with a Dew Point of 20° C. or Higher)

The step (c) is a step in which the glass sheet prepared in the step (a) is subjected to an ion exchange treatment (chemical strengthening treatment) using the molten salt prepared in the step (b). The chemical strengthening treatment is carried out by immersing the glass sheet into the molten salt to thereby achieve ion exchange (substitution) between the alkali ions (Li ions or Na ions) in the glass and the other alkali ions (Na ions or K ions) with larger ionic radii in the molten salt. Owing to the ion exchange, the composition of the glass sheet surface can be changed to form a compressive stress layer 20 in which the density in the glass sheet surface has increased ((a) and (b) of FIG. 2). By the increase of the density in the glass sheet surface, a compressive stress is generated so that the glass sheet can be strengthened.

Incidentally, in fact, the density of the chemically strengthened glass is gradually increased from an outer edge of an intermediate layer 30 (bulk) located at the center of the glass sheet toward the surface of the compressive stress layer. Therefore, between the intermediate layer 30 and the compressive stress layer 20, there is no clear boundary where the density varies suddenly. Here, the intermediate layer designates a layer which is located in a central portion of the glass sheet and between compressive stress layers on the opposite sides. Differently from the compressive stress layer, the intermediate layer is a layer which has not been subjected to the ion exchange.

Specifically the chemical strengthening treatment (ion exchange treatment) can be performed in the following procedure. First, the glass sheet is preheated, and the aforementioned molten salt is adjusted to a temperature for chemical strengthening. Next, the preheated glass sheet is immersed into the molten salt in a molten salt bath for a predetermined time. The glass sheet is then lifted up from the molten salt, and cooled. Incidentally, it is preferable that the glass sheet is subjected to profiling, for example, mechanical processing such as cutting, end face processing and perforating, in accordance with its usage before the chemical strengthening treatment.

It is preferable that the temperature of the chemical strengthening is not higher than the strain point (normally 500 to 600° C.) of the glass to be strengthened. Particularly in order to obtain a larger depth of the compressive stress layer, the temperature is preferably 350° C. or higher. In order to shorten the treatment time and accelerate the formation of a low density layer, the temperature is more preferably 400° C. or higher, and further more preferably 430° C. or higher.

In the method for manufacturing the chemically strengthened glass according to the present invention, the water vapor content in the molten salt when the glass sheet is dipped therein is increased, so that a low density layer formed in a step in which the glass sheet is brought into contact with acid as will be described later can be thickened. In a step in which the glass sheet is brought into contact with alkali, the low density layer can be removed. Therefore, when the thickness of the low density layer is made equal to or larger than the average depth of cracks or latent scratches existing in the glass sheet surface, the cracks or the latent scratches can be removed together with the removal of the low density layer. Thus, the excellent surface strength can be achieved in the chemically strengthened glass.

The step of performing the ion exchange is preferably performed in an atmosphere whose dew point temperature is 20° C. or higher. The dew point temperature is more preferably 30° C. or higher, even more preferably 40° C. or higher, particularly preferably 50° C. or higher, and most preferably 60° C. or higher. In addition, it is preferable that the upper limit of the dew point temperature is made not higher than the temperature of the inorganic salt (molten salt) with which the ion exchange is carried out.

As for the dew point temperature (hereinafter also referred to as "dew point" simply), the dew point temperature at least in the vicinity of the boundary surface of the molten salt may be within the aforementioned range. The vicinity of the boundary surface means an atmosphere in a region of 200 mm or less away from the boundary surface of the molten salt. The dew point can be measured by Vaisala DRYCAP (registered trademark) Dewpoint Transmitter DMT346. Incidentally, the dew point in the present description is a value when it is assumed that an equilibrium is established between the molten salt and the atmosphere in the vicinity of the boundary surface of the molten salt.

The aforementioned dew point can be achieved when water vapor is introduced into the molten salt and/or the atmosphere in the vicinity of the boundary surface of the molten salt before the step of performing the ion exchange and/or at the same time as the step of performing the ion exchange. For example, a water vapor supply portion is added to the molten salt bath so that water vapor can be introduced into the molten salt and/or the atmosphere in the vicinity of the boundary surface of the molten salt.

That is, water vapor supplied by the water vapor supply portion or gas including the water vapor, and water (liquid) may be introduced into the molten salt directly with bubbling, or the water vapor or the gas including the water vapor may be introduced into a space above the molten salt. In addition, water (liquid) itself can be dropped and introduced onto the molten salt within an extent not causing phreatic explosion.

When the water vapor, the gas including the water vapor or the water (liquid) (hereinafter also referred to as "water vapor etc." simply) is introduced, the molten salt does not have to be stirred, but it is preferable to stir the molten salt in order to shorten the time until reaching the equilibrium.

The time since the introduction of the water vapor etc. and until reaching the equilibrium cannot be said definitely. The time depends on the amount of the introduced gas or liquid, the concentration of the water vapor, the method of the introduction, etc. However, when the dew point of the aforementioned atmosphere is stable and constant, it can be determined that the equilibrium has been established.

Figure 3:
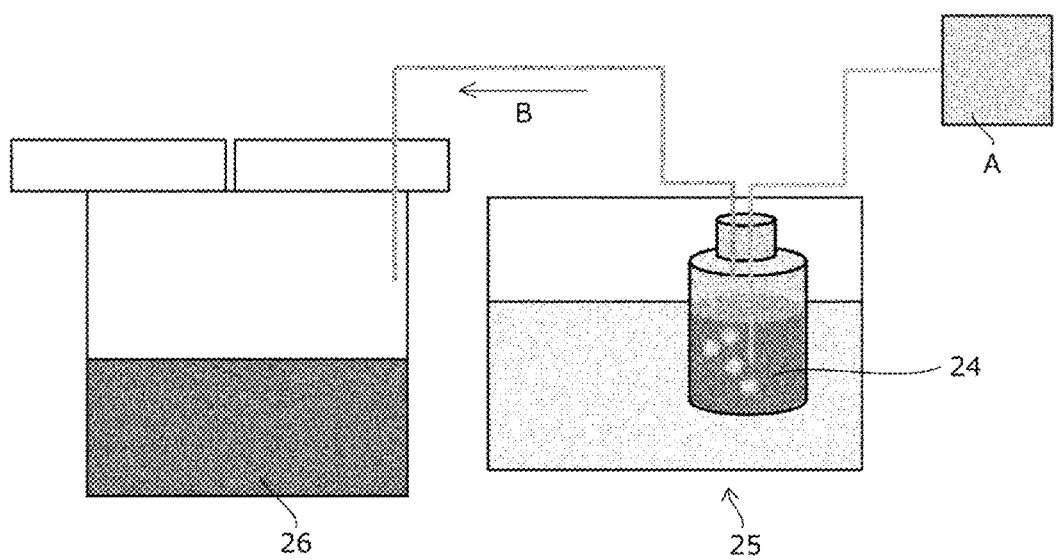
FIG. 3 is a schematic view of an experimental system for making an atmosphere in a chemical strengthening treatment.

As for the gas including the water vapor, a gas which has no influence on the chemical strengthening treatment can be used. For example, when a dry gas A such as the air, nitrogen gas, carbon dioxide gas, etc. is introduced into heated water 24 as shown in FIG. 3, a high-humidity gas including water vapor (gas including water vapor) B can be formed.

As the water 24 serving as a water vapor supply source, pure water such as ion-exchanged water is preferably used in order to suppress scales from depositing on a pipe or the like. The water 24 is, for example, heated by a water bath or the like using a water tank 25. In addition, the water 24 itself may be heated, for example, by a boiler or the like so that the water vapor can be generated.

More specific examples of the method for introducing the water vapor etc. include (1) introducing the gas B including water vapor into a space above the inorganic salt (molten salt 26) from the water vapor supply portion, (2) introducing the gas B including water vapor into the inorganic salt (molten salt 26) from a bubbling portion, (3) introducing water (liquid) directly to the inorganic salt (molten salt 26), etc. Among them, it is preferable that the atmosphere is formed by the method (1) or (2).

As a form for introducing the gas B including water vapor into the space above the inorganic salt (molten salt 26), there is, for example, a method in which the water vapor etc. supplied from the water vapor supply portion is sprayed to above the inorganic salt or to the vicinity of the boundary surface of the inorganic salt by a spray. Introducing the water vapor etc. by the spray is preferred because it makes it easy to control the water vapor concentration to be substantially uniform in the space above the inorganic salt.

Incidentally, the water vapor supply portion, the bubbling portion, the introduction portion for introducing water (liquid), or the spray is not particularly limited, but may be provided suitably in accordance with the apparatus. Specifically, as for the spray, either a single spray or a plurality of sprays may be provided. Particularly when the molten salt bath is large in size, the water vapor etc. may be sprayed by a plurality of sprays so as to make it easy to control the water vapor concentration to be substantially uniform in the space above the inorganic salt.

The reason why the surface strength of the obtained chemically strengthened glass is enhanced by the step of ion exchange performed in the molten salt rich in water vapor content (moisture content) can be considered as follows.

When carbonate ions forming the molten salt react with water, hydrogen carbonate ions and hydroxide ions are generated as shown in the following formula.

$$CO_3^{2-}+H_2O \leftrightarrow HCO_3^-+OH^-$$ [Chemical Formula 1]

Here, when the molten salt is rich in moisture content, the equilibrium in the aforementioned formula leans to the right to produce many hydrogen carbonate ions and hydroxide ions. The hydroxide ions are ions promoting cutting of the glass network. Accordingly, it is considered that formation of a low density layer which will be described later is promoted in the glass surface due to the production of more hydroxide ions The sum of a carbonate anion concentration and a hydrogen carbonate anion concentration in the inorganic salt obtained by the following expression is preferably 4 mol % or higher, and more preferably 6 mol % or higher. The concentration is preferably 4 mol % or higher, because reaction to form a low density layer in the glass surface can be promoted.

{(carbonate anion concentration)+(hydrogen carbonate anion concentration)} (mol %)={(carbonate anion content in inorganic salt)+(hydrogen carbonate anion content in inorganic salt)} (mol)/ {(total anion content in inorganic salt) (mol)× 100

Incidentally, the carbonate anion concentration and the hydrogen carbonate anion concentration in the molten salt cannot be measured directly. Therefore, a part of the molten salt is taken out. A commercially available standard solution (NaHCO$_3$) is diluted with pure water, and a calibration curve is created by use of a carbon dioxide meter TiN-9004. After that, a sample solution in which the molten salt which has been taken out is diluted with pure water by 130 times is measured. On this occasion, all the hydrogen carbonate anions are converted into carbonate anions. Therefore, the value of the carbonate anion concentration detected by the measurement corresponds to the sum of the carbonate anion concentration and the hydrogen carbonate anion concentration.

In addition, the sum of the carbonate anion concentration and the hydrogen carbonate anion concentration is not higher than the sum of a saturated carbonate anion concentration and a saturated hydrogen carbonate anion concentration.

The low density layer is formed in, of the step of removing a part of the surface of the glass sheet as will be described later, a step of bringing the glass sheet into contact with acid. The thickness of the low density layer can be increased to 300 nm or more by ion exchange in the atmosphere whose dew point temperature reaches 20° C. or higher owing to the introduction of water vapor, as compared with about 100 to 200 nm in a conventional ion exchange step where water vapor is not introduced.

In a glass sheet manufacturing process or a glass sheet processing process including a chemical strengthening treatment step, an average depth of cracks or latent scratches generated in the glass sheet surface is about 500 nm. Therefore, the thickness of the low density layer is more preferably 500 nm or more, and even more preferably 600 nm or more.

The formed low density layer can be removed in, of the step of removing a part of the surface of the glass sheet, a step of bringing the glass sheet into contact with alkali as will be described later. Therefore, if the depth of all the cracks and the latent scratches in the glass sheet surface are shallower than the thickness of the low density layer, all the cracks and the latent scratches can be removed in the step of bringing the glass sheet into contact with alkali.

When the cracks and the latent scratches in the glass sheet surface causing deterioration of strength in the chemically strengthened glass are removed, the surface strength of the chemically strengthened glass can be further enhanced.

It is preferable that a step of washing the glass sheet is further included between the step of performing the ion exchange and the step of removing a part of the surface of the glass sheet. In the washing step, the glass is washed with industrial water, ion-exchanged water, etc. When industrial water is used, it is treated in accordance with necessity. Among them, ion-exchanged water is preferred.

The washing conditions depend on a washing solution to be used therefor. When ion-exchanged water is used, it is preferable to perform washing at 0 to 100° C. in order to remove the adhering salt perfectly.

In the washing step, various methods can be used. Examples of the methods include a method in which the chemically strengthened glass is immersed in a water tank where the ion-exchanged water or the like has been put, a method in which the glass sheet surface is exposed to running water, a method in which a washing solution is sprayed toward the glass sheet surface by a shower, etc.

((d) Step of Removing a Part of the Ion-Exchanged Surface of the Glass Sheet)

Figure 2:
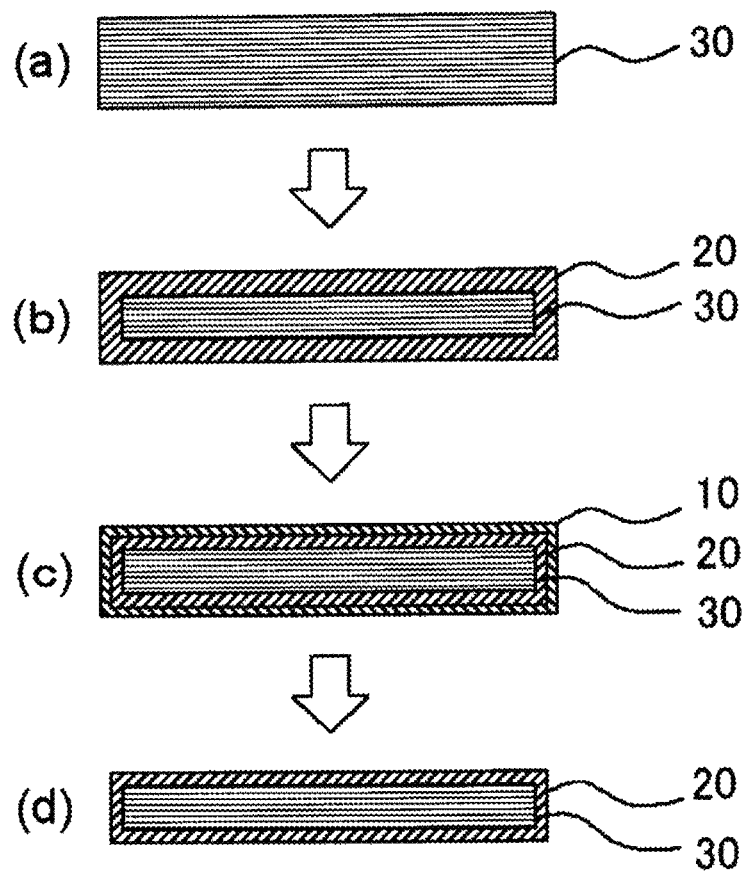
FIG. 2 is a schematic view showing steps of manufacturing a chemically strengthened glass according to the present invention.

The ion-exchanged glass sheet is subjected to the step of removing a part of the surface of the glass sheet ((c) to (d) of FIG. 2). It is preferable that the step of removing a part of the surface of the glass sheet includes a step of bringing the glass sheet into contact with acid. It is more preferable that the step of removing a part of the surface of the glass sheet further includes a step of bringing the glass sheet into contact with alkali after the step of bringing the glass sheet into contact with acid.

(Step of Bringing the Glass Sheet into Contact with Acid)

In the method for manufacturing the chemically strengthened glass according to the present invention, it is preferable that the step for bringing the glass sheet into contact with acid (acid treatment step) is performed after the ion exchange step or the washing step, as the step of removing a part of the surface of the glass sheet.

An acid treatment on the glass sheet is performed by immersing the chemically strengthened glass into an acidic solution so that Na and/or K in the chemically strengthened glass surface can be replaced by H. That is, the glass sheet surface can further include a low density layer in which a surface layer of the compressive stress layer is modified, specifically, reduced in density.

The solution is not particularly limited as long as it is acidic. As long as the pH is lower than 7.0, acid used as the solution is either weakly acidic or strongly acidic. Specifically, preferred examples of the solution include acids such as hydrochloric acid, nitric acid, sulfuric acid, phosphoric acid, acetic acid, oxalic acid, carbonic acid, citric acid, etc. One of those acids may be used alone, or a plurality of them may be used in combination.

The low density layer is removed by the alkali treatment which will be described later. Therefore, as the low density layer is thicker, the glass surface can be removed easily. The thickness of the low density layer has been described previously. From the viewpoint of the removal amount of the glass sheet surface, the thickness is preferably 300 nm or more, more preferably 500 nm or more, and even more preferably 600 nm or more.

From the viewpoint of removability of the glass sheet surface, the density of the low density layer is lower than the density of the region (bulk) deeper than the compressive stress layer subjected to the ion exchange. The thickness of the low density layer can be obtained from a cycle ($\Delta\theta$) measured by XRR (X-ray-Reflectometry). The density of the low density layer can be obtained from a critical angle ($\theta c$) measured by the XRR.

Incidentally, in a simple manner, the formation of the low density layer and the thickness of the layer can be also confirmed by sectional observation of the glass with a scanning electron microscope (SEM).

(Step of Bringing the Glass Sheet into Contact with Alkali)

In the method for manufacturing the chemically strengthened glass according to the present invention, it is preferable that a step of bringing the glass sheet into contact with alkali (alkali treatment step) is further performed after the step of bringing the glass sheet into contact with acid. It is more preferable that a step of washing the glass sheet in the same manner as the aforementioned washing step is performed after the step of bringing the glass sheet into contact with acid and before the step of bringing the glass sheet into contact with alkali.

An alkali treatment is performed by immersing the chemically strengthened glass into a basic solution so that a part or all of the low density layer formed in the step of bringing the glass sheet into contact with acid can be removed.

The solution is not particularly limited as long as it is basic. As long as the pH exceeds 7.0, either weak base or strong base may be used. Specifically, preferred examples of the solution include bases such as sodium hydroxide, potassium hydroxide, potassium carbonate, sodium carbonate, etc. One of those bases may be used alone, or a plurality of them may be used in combination.

Owing to the aforementioned alkali treatment, a part or all of the low density layer intruded by H is removed. Thus, a chemically strengthened glass whose surface strength has been improved can be obtained. Particularly in the method for manufacturing the chemically strengthened glass according to the present invention, the thickness of the low density layer can be formed to be deeper than the depth of cracks or latent scratches existing in the glass sheet surface. It is therefore considered that the cracks or the latent scratches existing in the glass sheet surface can be removed together with the low density layer so as to further contribute to the improvement of the surface strength of the glass. Incidentally, it is preferable that a step of washing the glass sheet in the same manner as described previously is also performed after the alkali treatment.

EXAMPLES

Examples will be illustrated below for explaining the present invention specifically. However, the present invention is not limited to those Examples.

<Evaluation Method>

Various evaluations in these Examples were performed in the following analysis methods.

(Removal Amount)

The removal amount thickness of the glass sheet was obtained by measuring weights before and after the chemical treatment described below by an analytical electronic balance (HR-202 i, made by A&D Company, Limited) and converting the weights into thickness by means of the expression below. At this time, the specific gravity of the glass was taken as 2.46 ($g/cm^3$) for the calculation.

(thickness of removal amount per side)=((weight before treatment)−(weight after treatment))/ (glass specific gravity)/treated area/2

Chemical Treatment: 6.0 weight % nitric acid (Nitric Acid 1.38 (made by Kanto Chemical Co., Ltd.) was diluted with ion-exchanged water) and 4.0 weight % sodium hydroxide aqueous solution (48% sodium hydroxide aqueous solution (made by Kanto Chemical Co., Ltd.) was diluted with ion-exchanged water) were prepared in beakers respectively, and their temperatures were adjusted to 40° C. by use of a water bath. A chemically strengthened glass obtained by a chemical strengthening treatment was immersed in the prepared nitric acid for 120 seconds so as to be subjected to an acid treatment. After that, the glass was washed with pure water several times, and then immersed in the prepared sodium hydroxide aqueous solution for 120 seconds so as to be subjected to an alkali treatment. After that, the glass was washed with water to thereby wash out alkali from the glass sheet surface. After that, the glass was dried by air blowing.

(Surface Stress)

The surface compressive stress value (CS in units of MPa) and the depth of the compressive stress layer (DOL in units of $\mu m$) in the glass sheet were measured by use of a surface stress meter (FSM-6000) made by Orihara Industrial Co., Ltd.

(Hydrogen Concentration)

According to the method described in the aforementioned (Method for Measuring Hydrogen Concentration Profile), a hydrogen concentration profile was measured, and Expression (I) was derived therefrom.

(Surface Strength)

The surface strength of the glass sheet was measured by a ball-on-ring strength test. FIG. 1 shows a schematic view for explaining the ball-on-ring strength test used in the present invention. A glass sheet 1 which had been mounted horizontally was pressurized by use of a pressure jig 2 (made of quenched steel, having a diameter of 10 mm, and mirror-finished) made of SUS304 to measure the surface strength of the glass sheet.

In FIG. 1, the glass sheet which served as a sample was placed horizontally on a reception jig 3 (having a diameter of 30 mm, including a contact portion having a curvature radius R of 2.5 mm and made of quenched steel, and mirror-finished) made of SUS304. The pressure jig 2 for pressurizing the glass sheet was placed above the glass sheet.

In these Examples, the central region of the obtained glass sheet was pressurized from above the glass sheet. Incidentally, test conditions will be described below.

Descending Rate of Pressure Jig: 1.0 (mm/min)

On this occasion, a breaking load (in units of N) with which the glass sheet was broken was regarded as BoR surface strength, and an average value of BoR surface strength measured 20 times was regarded as BoR average surface strength. When a breaking start point of the glass sheet was 2 mm or more away from the position where the ball was pressed, the measured BoR surface strength was excluded from data for calculating the average value.

(Rubber Eraser Abrasion Test)

A rubber eraser abrasion test was performed in the following method to measure the AFP abrasion resistance.

The chemically strengthened glass sheet surface was cleaned by ultraviolet rays, and sprayed and coated with OPTOOL (registered trademark) DSX (made by Daikin Industries, Ltd.) so as to form an AFP film substantially uniformly on the glass sheet surface. The AFP film was formed such that the thickness thereof was about 7.0 to 10.0 nm. The AFP film was treated and hardened under the conditions of 50° C. and 80% RH for 1 hour.

A tester (plane abrasion tester (triple type) model: PA-300A made by Daiei Kagaku Seiki Mfg. Co., Ltd.) was used, and a rubber eraser (MINOAN™ made by Mirae Science Co., Ltd.) was attached to an indenter with 1 cm² wide. In a state where a load of 1 kgf was applied to the rubber eraser, the surface of the AFP film formed on the glass sheet surface was rubbed with the rubber eraser reciprocatively 4,000 times with a stroke width of 20 mm and at a velocity of 30 mm/sec. After that, the AFP film surface was dry-wiped and cleaned with a cloth (DUSPER (registered trademark) made by Ozu Corporation). Then, water contact angles (°) were measured at three places on the AFP film surface. This operation was repeated three times, and an average water contact angle (°) was measured from the total of nine water contact angles. The water contact angles (°) on the AFP film surface were measured by a method according to JIS R 3257 (1999).

(Surface Roughness)

The surface roughness of the glass sheet was measured by surface observation under the following conditions by use of an AFM.

Measuring Range: 1 μm×0.5 μm
Apparatus: Nanoscope V+MultiMode 8 or Dimension ICON made by Bruker Corporation
Mode; ScanAsyst
Mode Probe: RTESPA (spring constant: 40 N/m)
Samples/Line: 256
Lines: 128
Scan Rate: 1 Hz
Measuring Field: 1×0.5 μm² (aiming at a place free from contamination)

<Preparation of Chemically Strengthened Glass>

The following compositions of glasses were used in Examples and Comparative Examples.

Glass Sheet A (expressed by mol % on an oxide basis): 64.4% of $SiO_2$, 10.5% of $Al_2O_3$, 16.0% of $Na_2O$, 0.6% of $K_2O$, 8.3% of MgO, and 0.2% of $ZrO_2$ Glass Sheet B (expressed by mol % on an oxide basis): 67.0% of $SiO_2$, 13.0% of $Al_2O_3$, 14.0% of $Na_2O$, 4.0% of $B_2O_3$, less than 1.0% of $K_2O$, 2.0% of MgO, and less than 1.0% of CaO Example 1

9,047 g of potassium nitrate, 805 g of potassium carbonate and 148 g of sodium nitrate were added to a pot made of stainless steel (SUS), and heated to 450° C. by a mantle heater to thereby prepare a molten salt having 6 mol % of potassium carbonate and 4,000 weight ppm of sodium. The air introduced into water heated to 89° C. was made to flow into an atmosphere in the vicinity of the boundary surface of the molten salt to thereby make the molten salt contain water vapor.

FIG. 3 shows an apparatus used for manufacturing a chemically strengthened glass according to the present invention. The air was used as a dry gas A. The air was passed into water 24 heated to 89° C. by a water tank 25 so as to be humidified. Thus, a humidified gas (air) B containing water vapor was formed.

Via a path heated by a ribbon heater, the gas B containing water vapor was introduced into a space above inorganic salt (molten salt) 26 in a bath for chemical strengthening treatment. Thus, the dew point in the step of ion exchange treatment was controlled. On this occasion, the water vapor supply rate was 3 L/min, and the dew point in the vicinity of the boundary surface of the molten salt was 40° C.

The glass sheet A measuring 50 mm by 50 mm with a thickness of 0.7 mm was prepared and preheated to 350 to 400° C. Then the glass sheet A was immersed in the molten salt at 450° C. for 90 minutes so as to be subjected to an ion exchange treatment. After that, the glass sheet A was cooled down to the vicinity of a room temperature. Thus, a chemical strengthening treatment was performed. The obtained chemically strengthened glass was washed with water, and subjected to the following step.

(Acid Treatment Step)

6.0 weight % of nitric acid (Nitric Acid 1.38 (made by Kanto Chemical Co., Ltd.) was diluted with ion-exchanged water) was prepared in a beaker, and the temperature thereof was adjusted to 40° C. by use of a water bath. The chemically strengthened glass obtained by the aforementioned chemical strengthening treatment was immersed in the prepared nitric acid for 120 seconds so as to be subjected to acid treatment. After that, the chemically strengthened glass was washed with water, and subjected to the following step.

(Alkali Treatment Step)

4.0 weight % of sodium hydroxide aqueous solution (48% sodium hydroxide aqueous solution (made by Kanto Chemical Co., Ltd.) was diluted with ion-exchanged water) was prepared in a beaker, and the temperature thereof was adjusted to 40° C. by use of a water bath. The chemically strengthened glass washed with water after the step of bringing the glass sheet into contact with acid was immersed in the prepared sodium hydroxide aqueous solution for 120 seconds so as to be subjected to an alkali treatment. After that, the chemically strengthened glass was washed with water to thereby wash out alkali from the chemically strengthened glass surface. After that, the chemically strengthened glass was dried by air blowing.

The chemically strengthened glass of Example 1 was thus obtained.

Example 2

A chemically strengthened glass was manufactured in the same manner as in Example 1, except for the conditions of the chemical strengthening treatment (ion exchange treatment) in which the air was passed through water heated to 99° C. to humidify an atmosphere in the vicinity of the boundary surface of the molten salt, and the humidified gas containing water vapor was introduced into a space above the inorganic salt (molten salt) in the bath for chemical strengthening treatment so that the dew point in the vicinity of the boundary surface of the molten salt was set at 66° C.

Example 3

A chemically strengthened glass was manufactured in the same manner as in Example 1, except that the glass sheet B measuring 50 mm by 50 mm with a thickness of 0.55 mm was used.

Example 4

A chemically strengthened glass was manufactured in the same manner as in Example 2, except that the glass sheet B measuring 50 mm by 50 mm with a thickness of 0.55 mm was used.

Comparative Example 1 and 2

Chemically strengthened glasses were manufactured in the same manner as in Example 1, except that the glass sheet A and the glass sheet B were used, and the chemical strengthening treatment (ion exchange treatment) was performed on the conditions in which the molten salt for the chemical strengthening treatment did not contain $K_2CO_3$ as shown in Table 1, the acid treatment and the alkali treatment were not performed, and the dew point was not controlled to reach 20° C. or higher.

Various evaluations were performed on the chemically strengthened glasses obtained thus. The treatment conditions and the evaluation results of the glasses are shown in Table 1, FIG. 4A and FIG. 4B. Incidentally, BoR average surface strength is shown as the BoR surface strength.

The chemically strengthened glass according to the present invention is typically obtained by a chemical strengthening treatment in which a dew point is controlled. In the chemically strengthened glass according to the present invention thus obtained, the hydrogen concentration in the glass sheet surface layer is within a specific range. When a glass has a high hydrogen concentration, hydrogen enters an Si—O—Si bond network of the glass to form Si—OH bond. Thus, the Si—O—Si bond is disconnected. As the hydrogen concentration in the glass is higher, parts where the Si—O—Si bond is disconnected are increased. The generated parts where the Si—O—Si bond is disconnected can serve as bonding start points with an AFP agent. Accordingly, when the hydrogen concentration in the glass sheet surface layer is within a specific range, it is considered that parts forming bonds with the AFP agents can be increased. Thus, it is considered that a plenty of the AFP agent remains in the glass sheet surface even after an AFP abrasion resistance test, so that the contact angle can be kept high. In this manner, it is considered that the chemically strengthened glass according to the present invention has a high AFP abrasion resistance.

TABLE 1

| | | | Ex. 1 | Ex. 2 | Comp. Ex. 1 | Ex. 3 | Ex. 4 | Comp. Ex. 2 |
|---|---|---|---|---|---|---|---|---|
| glass material | | | glass A | glass A | glass A | glass B | glass B | glass B |
| sheet thickness | | mm | 0.7 | 0.7 | 0.7 | 0.55 | 0.55 | 0.55 |
| salt composition | $K_2CO_3$ | mol % | 6 | 6 | — | 6 | 6 | — |
| | Na | weight ppm | 4000 | 4000 | 2000 | 4000 | 4000 | 2000 |
| chemical strengthening treatment | dew point | ° C. | 40 | 66 | 15 | 40 | 66 | 15 |
| | temperature/time | ° C./hr | 450/1.5 | 450/1.5 | 450/1.5 | 450/1.5 | 450/1.5 | 450/1.5 |
| | acid treatment and alkali treatment | | yes | yes | no | yes | yes | no |
| | removal amount | nm/side | 420 | 603 | — | 680 | 1190 | — |
| CS/DOL | CS | MPa | 969 | 962 | 995 | 806 | 800 | 830 |
| | DOL | μm | 27 | 28 | 27 | 32 | 32 | 32 |
| SIMS | value a | | −0.371 | −0.349 | −0.279 | −0.312 | −0.434 | −0.213 |
| | value b | | 0.311 | 0.301 | 0.219 | 0.365 | 0.324 | 0.239 |
| surface strength | Ave. | N | 1019 | 1065 | 500 | 661 | 504 | 355 |
| | $F/t^2$ | | 2030 | 2174 | 1019 | 2186 | 1706 | 1174 |
| AFP abrasion resistance | 0 time | contact angle | ° | 114.5 | 114.9 | 113.9 | 115.0 | 114.8 | 114.7 |
| | 2000 times | | ° | 107.9 | 102.7 | 89.6 | 103.6 | 105.1 | 102.2 |
| | 4000 times | | ° | 101.2 | 93.6 | 43.1 | 99.0 | 100.2 | 60.0 |
| | 6000 times | | ° | 93.2 | 89.3 | 38.4 | 89.9 | 92.1 | 39.4 |
| surface roughness Ra | | nm | 0.57 | 0.55 | 0.17 | 0.72 | 0.73 | 0.19 |

Figure 4A:
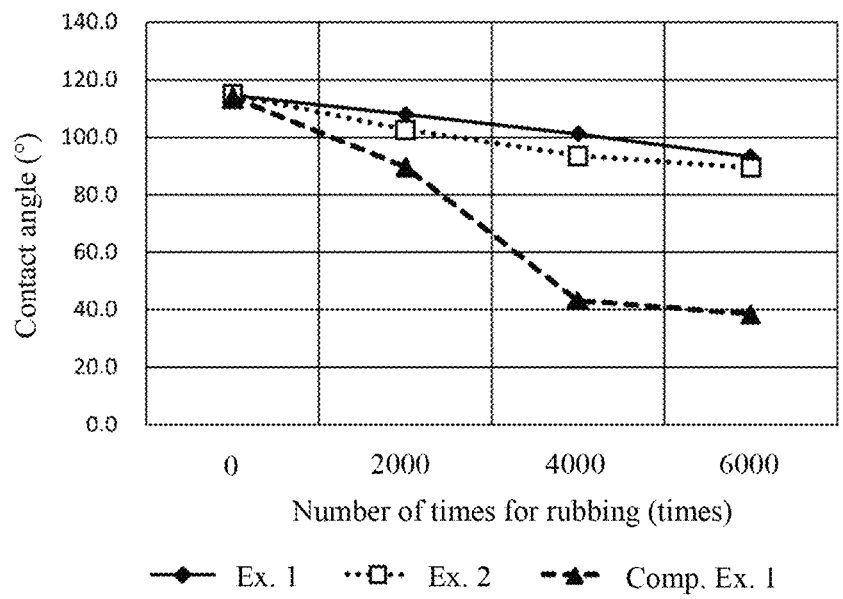
FIG. 4A and FIG. 4B are graphs showing results of AFP abrasion resistance evaluated by a rubber eraser abrasion test.

As shown in Table 1 and FIG. 4A, in Example 1 and Example 2 which were chemically strengthened glasses according to the present invention, the surface strength was improved conspicuously, and the AFP abrasion resistance was improved conspicuously, as compared with those in Comparative Example 1 which was a chemically strengthened glass obtained by a normal chemical strengthening treatment.

Figure 4B:
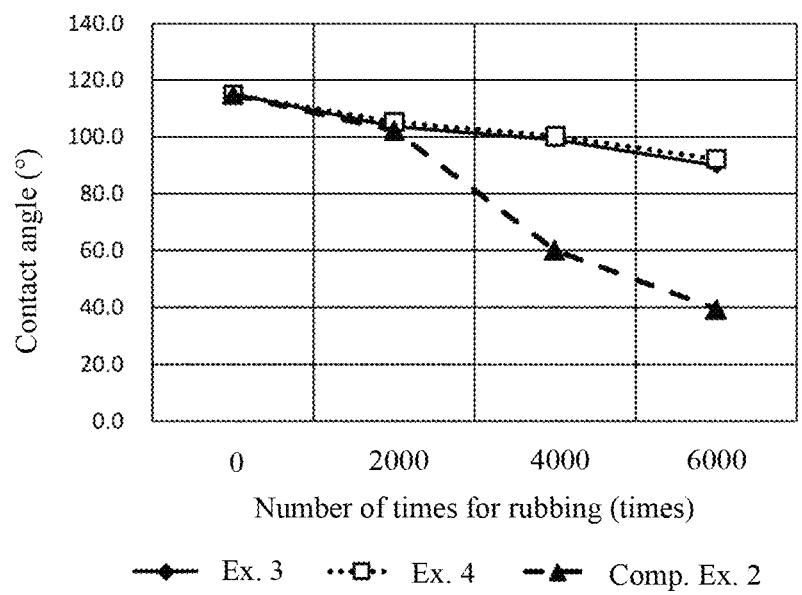

As shown in Table 1 and FIG. 4B, in Example 3 and Example 4 which were chemically strengthened glasses according to the present invention, the surface strength was improved conspicuously, and the AFP abrasion resistance was improved conspicuously, as compared with those in Comparative Example 2 which was a chemically strengthened glass obtained by a normal chemical strengthening treatment.

From those results, a chemically strengthened glass according to the present invention in which a hydrogen concentration profile in a glass sheet surface layer is within a specific range is a chemically strengthened glass capable of attaining the surface strength and the AFP abrasion resistance compatibly.

Incidentally, any glass shows a similar contact angle before the AFP abrasion resistance test (0 time). It is considered that this is because the AFP agent is saturated so that some pieces of the AFP agent are not bonded with the glass but are bonded with each other.

The chemically strengthened glass according to the present invention is typically obtained by the chemical strengthening treatment in which a dew point is controlled. In the chemically strengthened glass according to the present invention obtained thus, the surface roughness (Ra) is 0.30 nm or more. Accordingly, it is considered that the surface roughness is higher than in the chemically strengthened glass obtained by the conventional chemical strengthening treatment, and thus contact points with a rubber eraser are reduced so that the AFP abrasion resistance is improved. In the chemically strengthened glass according to the present invention, the surface roughness (Ra) is about 0.90 nm or less. Therefore, transparency can be also kept on the appearance of the glass sheet.

In the chemically strengthened glass according to the present invention, the hydrogen concentration in the glass is within a specific range so that hydrogen enters the Si—O—

Si bond network of the glass to form Si—OH bond to thereby disconnect the Si—O—Si bond. However, the range of the hydrogen concentration is not high enough to cause conspicuous deterioration in surface strength. Therefore, owing to the hydrogen concentration in the glass sheet surface layer within the specific range, the surface strength can be kept high, and the AFP abrasion resistance can be enhanced.

Although the present invention has been described in detail with reference to its specific embodiments, it is obvious for those skilled in the art that various changes and modifications can be made without departing from the spirit and scope of the present invention. The present application is based on a Japanese patent application (Patent Application No. 2017-123365) filed on Jun. 23, 2017, the entire contents of which are incorporated herein by reference. In addition, all the references cited herein are incorporated entirely.

INDUSTRIAL APPLICABILITY

A chemically strengthened glass according to the present invention is a chemically strengthened glass very high in surface strength and excellent in AFP abrasion resistance. Therefore, the chemically strengthened glass can be, for example, used suitably as a cover glass for use in a display device.

REFERENCE SIGNS LIST 1 glass sheet
2 pressure jig
3 reception jig
10 low density layer
20 compressive stress layer
30 intermediate layer
24 water
25 water tank
26 molten salt

The invention claimed is:

1. A chemically strengthened glass having a sheet shape and comprising a compressive stress layer in a glass surface layer and having a sheet thickness of 0.7 mm or more, wherein:
  a straight line linearly approximating a profile of a hydrogen concentration Y with respect to a depth X from an outermost surface of a glass sheet at X=0.1 to 0.6 (μm) satisfies Expression (I);
  a surface strength F (N) measured on conditions below by a ball-on-ring strength test is 1019 N or more; and
  a contact angle is 65° or more after 4,000 times of an abrasion when an AFP abrasion resistance is measured on conditions below by a rubber eraser abrasion test:

$$Y=aX+b \quad (I),$$

wherein:
  Y is the hydrogen concentration (mol/L, measured as $H_2O$);
  X is the depth from the outermost surface of the glass sheet (μm);
  a is −0.450 to −0.300; and
  b is 0.250 to 0.400.

2. The chemically strengthened glass according to claim 1, having a surface roughness (Ra) of 0.30 nm or more.

3. The chemically strengthened glass according to claim 1, having a surface compressive stress value (CS) of 600 MPa or more.

4. The chemically strengthened glass according to claim 1, having a depth of the compressive stress layer (DOL) of 10 μm or more.

5. The chemically strengthened glass according to claim 1, having an internal tensile stress (CT) of 72 MPa or less.

6. A display device, comprising the chemically strengthened glass according to claim 1.

7. The chemically strengthened glass according to claim 1, having a glass composition comprising sodium.

8. The chemically strengthened glass according to claim 1, having a sheet thickness of 5 mm or less.

* * * * *